US011534516B2

(12) United States Patent
Kleinmann et al.

(10) Patent No.: US 11,534,516 B2
(45) Date of Patent: Dec. 27, 2022

(54) DECONTAMINATION ARRANGEMENT, SYSTEM AND DECONTAMINATION METHOD

(71) Applicant: Metall + Plastic GmbH, Radolfzell (DE)

(72) Inventors: Stefan Kleinmann, Radolfzell (DE); David Vertongen, Leuven (BE); Thomas Kassner, Radolfzell (DE)

(73) Assignee: METALL + PLASTIC GMBH, Radolfzell (DE)

( * ) Notice: Subject to any disclaimer, the term of this patent is extended or adjusted under 35 U.S.C. 154(b) by 270 days.

(21) Appl. No.: 16/617,579

(22) PCT Filed: Sep. 13, 2017

(86) PCT No.: PCT/EP2017/072964
§ 371 (c)(1),
(2) Date: Nov. 27, 2019

(87) PCT Pub. No.: WO2018/219482
PCT Pub. Date: Dec. 6, 2018

(65) Prior Publication Data
US 2020/0108163 A1  Apr. 9, 2020

(30) Foreign Application Priority Data
Jun. 1, 2017  (EP) .................................. 17174022

(51) Int. Cl.
| *A61L 2/20* | (2006.01) |
| *A61L 2/22* | (2006.01) |
| *A61L 9/015* | (2006.01) |

(52) U.S. Cl.
CPC ................. *A61L 2/208* (2013.01); *A61L 2/22* (2013.01); *A61L 9/015* (2013.01);
(Continued)

(58) Field of Classification Search
None
See application file for complete search history.

(56) References Cited

U.S. PATENT DOCUMENTS

| 5,288,467 | A | * | 2/1994 | Biermaier | ................. A61L 2/26 134/170 |
| 6,010,400 | A | | 1/2000 | Huza | |

(Continued)

FOREIGN PATENT DOCUMENTS

| DE | 102013102963 A1 | * | 9/2014 | ............. B67B 3/003 |
| DE | 102015106017 A1 | * | 10/2016 | ............... A61L 2/18 |

(Continued)

OTHER PUBLICATIONS

Leadley, Innovation and Future Trends in Food Manufacturing and Supply Chain Technologies, 2016, Elsevier Science (Year: 2016).*

(Continued)

*Primary Examiner* — Holly Kipouros
(74) *Attorney, Agent, or Firm* — Bachman & LaPointe, P.C.

(57) ABSTRACT

A decontamination assembly, for pharmaceutical applications includes at least one chamber to be decontaminated (4) having a decontamination liquid storage tank (36) by which several atomizers (A, B, C. D) disposed in the chamber to be decontaminated (4) for producing a decontaminant aerosol can be supplied with decontamination liquid using valves (27) which can be controlled by electronic control, the atomizers (A, B, C, D) being in fluid communication with a ring conduit (32) having an inlet (33) and a separate outlet (34) by the valves (27), decontamination liquid from the decontamination liquid storage tank (36) being conveyable into the inlet of the ring conduit by a pump (35) and decontamination liquid flowing out of the outlet of the ring conduit back into the decontamination liquid storage tank (36), and a pressure adjustment mechanism (37) for keeping (Continued)

the pressure in the ring conduit (32) at a predefined liquid pressure range assigned to the ring conduit (32). A measuring mechanism (40) for determining a total volume of decontamination liquid dispensed to the atomizers (A, B, C, D) during a decontamination cycle includes a weighing mechanism (41) for determining a decontamination liquid volume in the decontamination liquid storage tank (36).

23 Claims, 1 Drawing Sheet

(52) U.S. Cl.
CPC ...... *A61L 2202/11* (2013.01); *A61L 2202/122* (2013.01); *A61L 2202/14* (2013.01); *A61L 2209/135* (2013.01); *A61L 2209/14* (2013.01)

(56) References Cited

U.S. PATENT DOCUMENTS

| | | | | |
|---|---|---|---|---|
| 6,645,429 | B1* | 11/2003 | Raniwala | B65B 55/027 |
| | | | | 422/28 |
| 6,840,744 | B2 | 6/2005 | Watling | |
| 9,533,064 | B1* | 1/2017 | Adiga | A61L 9/14 |
| 2003/0143110 | A1* | 7/2003 | Kritzler | A61L 2/22 |
| | | | | 422/29 |
| 2003/0152481 | A1* | 8/2003 | Birnecker | A61L 2/18 |
| | | | | 422/28 |
| 2010/0038448 | A1* | 2/2010 | Ghavami-Nasr | B05B 1/3426 |
| | | | | 239/124 |
| 2010/0205907 | A1* | 8/2010 | Herold | A61L 2/24 |
| | | | | 53/167 |
| 2012/0230868 | A1* | 9/2012 | Reddy | A61L 2/07 |
| | | | | 422/26 |
| 2013/0004390 | A1 | 1/2013 | Hauk | |
| 2015/0329391 | A1* | 11/2015 | Garusi | C02F 1/76 |
| | | | | 210/739 |
| 2018/0229149 | A1* | 8/2018 | Spiegelman | A61L 2/20 |

FOREIGN PATENT DOCUMENTS

| | | |
|---|---|---|
| EP | 1764115 A1 | 3/2007 |
| EP | 2786811 A1 | 10/2014 |
| WO | 2011085735 A1 | 7/2011 |
| WO | 2013003967 A1 | 1/2013 |

OTHER PUBLICATIONS

International search report for patent application No. PCT/EP2017/072964 dated Nov. 24, 2017.

* cited by examiner

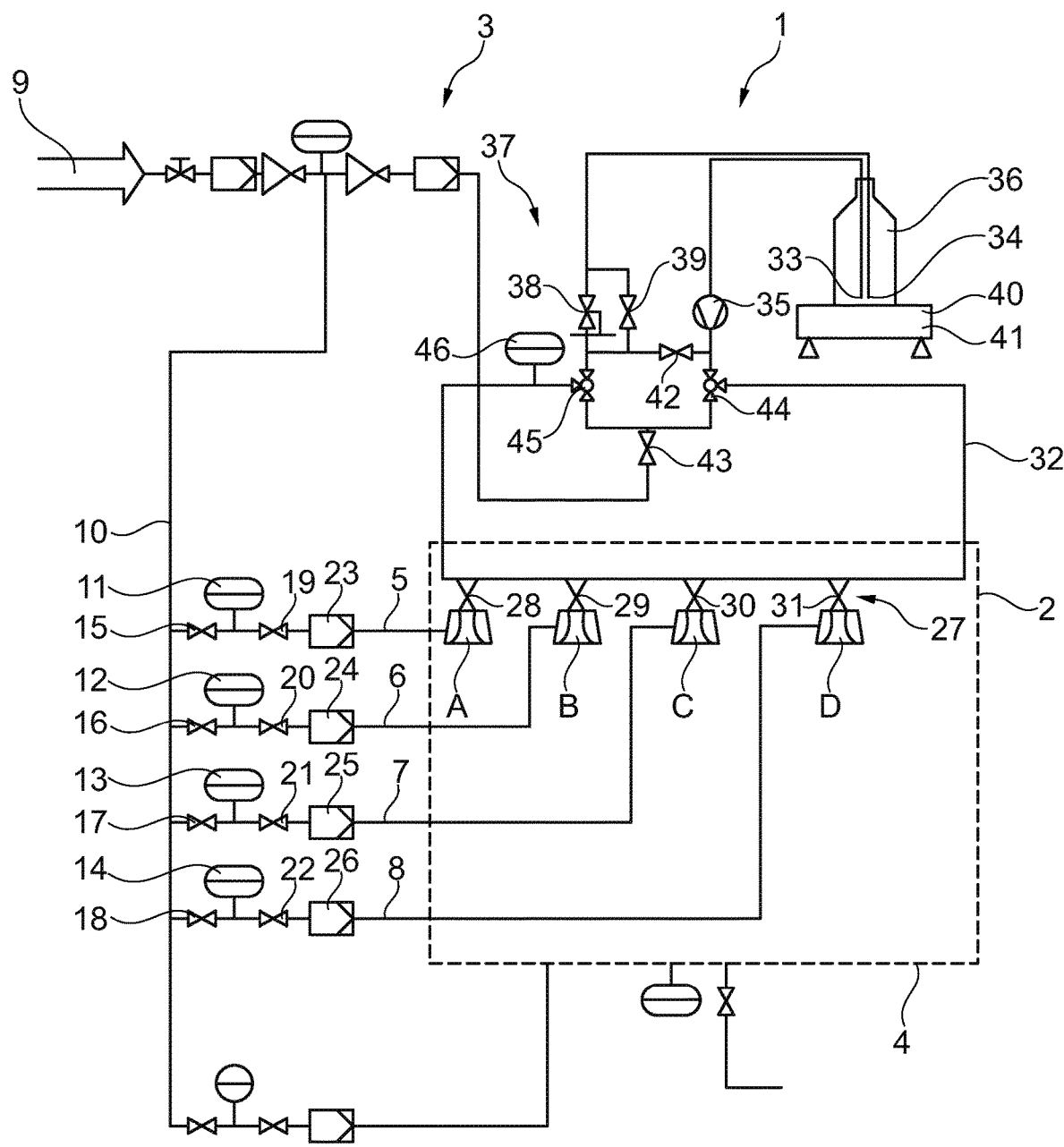

DECONTAMINATION ARRANGEMENT, SYSTEM AND DECONTAMINATION METHOD

BACKGROUND OF THE INVENTION

The invention relates to a decontamination assembly, in particular for pharmaceutical applications, the decontamination assembly comprising at least one chamber to be decontaminated, in particular an isolator chamber, preferably a manipulator chamber and/or a plenum chamber separated from the manipulator chamber by a membrane, comprising a decontamination liquid storage tank from which several atomizers disposed in the chamber to be decontaminated and preferably configured as two-component nozzles for producing a decontamination liquid aerosol, in particular a hydrogen peroxide aerosol, can be supplied with decontamination liquid, preferably hydrogen peroxide, using valve means which can be controlled by means of electronic control means, the atomizers being in fluid communication with a (common) ring conduit via the valve means, the ring conduit having an inlet and a separate outlet, decontamination liquid from the decontamination liquid storage tank being conveyable into the inlet of said ring conduit by means of a pump and decontamination liquid flowing out of the outlet of said ring conduit back into the decontamination liquid storage tank, and pressure adjustment means for keeping the liquid pressure in the ring conduit in a predefined liquid pressure range being assigned to the ring conduit.

Furthermore, the invention relates to a system comprising an isolator, preferably for pharmaceutical applications, comprising a chamber to be decontaminated, in particular a manipulator chamber and/or a plenum chamber separated from the manipulator chamber by a membrane for laminarizing an air flow of a circulation fan of the isolator, and comprising a decontamination assembly. The circulation fan is preferably disposed in a circulation generating chamber above the aforementioned plenum chamber. The manipulator chamber is particularly preferably connected in an air-conducting manner to the circulation generating chamber via a backflow channel which is more preferably realized between two transparent panes. For realizing the feature of the establishment of the isolator for pharmaceutical applications, a dosing and/or a filling device for a pharmaceutical ingredient and/or a production device for such an ingredient is preferably disposed in the manipulator chamber. In a particularly preferred embodiment, the manipulator chamber is accessible to an operator by means of gloves for a manual processing from the outside, the gloves or so-called glove ports being disposed or fixed in a lateral wall of the manipulator chamber.

Additionally, the invention relates to decontamination method, in particular for operating a decontamination assembly according to the invention and/or a system according to the invention, a chamber to be decontaminated, in particular an isolator chamber, preferably a manipulator chamber and/or plenum chamber separated from the manipulator chamber by a membrane, being decontaminated by producing a decontamination liquid aerosol from a decontamination liquid, in particular hydrogen peroxide, by means of atomizers which are disposed in the chamber to be decontaminated and which are preferably configured as two-component nozzles supplied with compressed air, said atomizers being supplied with the decontamination liquid from a decontamination liquid storage tank via valve means, the atomizers being in fluid communication with a ring conduit via the valve means, the ring conduit having an inlet and a separate outlet, decontamination liquid from the decontamination liquid storage tank being conveyed into the inlet of said ring conduit by means of a pump and decontamination liquid flowing out of the outlet of said ring conduit back into the decontamination liquid storage tank, in particular while decontamination liquid is being dispensed via the atomizers, a liquid pressure of the decontamination liquid in the ring conduit being kept in a predefined pressure range by means of pressure adjustment means, in particular by limiting a maximum fluid pressure.

Within the scope of the present disclosure, the feature of the supply of the atomizers by means of valve means is to be understood in such a manner that the decontamination liquid has to pass through or flow through corresponding valve means on the flow path from the decontamination liquid storage tank to the atomizers. The valve means can be controlled, in particular opened or closed, by control means (control device). More preferably, the valve means are configured in such a manner that a fluid communication between the atomizers and the decontamination liquid storage tank, particularly preferably a ring conduit which will be described below and which is provided according to the invention, can be interrupted by means of said valve means by a corresponding control by the control means.

WO 2011/085735 A1 or EP 2 719 962 A1 describes a decontamination assembly comprising a pharmaceutical isolator and an $H_2O_2$ evaporator. The $H_2O_2$ evaporator (flash evaporator) is directly connected via a supply line to a plenum chamber which is separated from a manipulator chamber located below by means of a membrane for generating a laminar air flow when the isolator is operated. During a decontamination phase, hydrogen peroxide vapor is introduced into the plenum chamber via the supply line, the hydrogen peroxide vapor moving through the membrane downwards into the manipulator chamber.

From U.S. Pat. No. 6,010,400 A, a method is known in which circulating air is conveyed through an evaporator, i.e. said evaporator is not supplied with sterile compressed air from the outside, the hydrogen peroxide vapor being directly introduced into a manipulator chamber without using a high efficiency particulate air filter which is impregnated with a catalyst in an area above the manipulator chamber.

WO 2013/003967 A1 describes a decontamination assembly in which the hydrogen peroxide is not vaporized in a conventional manner by means of a flash evaporator, but in which two-component nozzles are used in order to atomize the liquid hydrogen peroxide, i.e. to produce an aerosol. With respect to the known decontamination assembly, a decontamination liquid storage tank (reservoir) and the atomizer are an integral part of a device which can be installed as a whole in the chamber to be decontaminated.

In practice, there are also solutions in which several atomizers are connected to a common decontamination liquid storage tank via a supply line which ends at the corresponding atomizer. A pump and a valve are assigned to each supply line. Before the beginning of a decontamination cycle, the individual supply lines have to be filled using the respective pump; the actual decontamination cycle in which the decontamination liquid in the form of an aerosol is dispensed into the chamber to be decontaminated by means of the atomizers starts after said filling. The air inside the supply lines has to be dispensed into the chamber to be decontaminated by means of the atomizers. After completion of the decontamination cycle, the supply lines have to be emptied into the decontamination liquid storage tank in order to determine the total volume of decontamination liquid which has been dispensed by means of the atomizers; for this purpose, the conveyor pumps are operated in reverse. The total volume of used or dispensed decontamination liquid is determined by defining the difference between the weight of the storage tank before the filling of the supply lines and the weight of the storage tank after the decontamination cycle and the subsequent emptying of the supply lines. Concerning the known decontamination assembly or the known decontamination method, the laborious determination of the total volume of dispensed decontamination liquid which is needed for a validating decontamination process is disadvantageous because all supply lines have to be emptied again. Furthermore, detecting if all supply lines are actually filled completely with decontamination liquid before a decontamination cycle is laborious and prone to error. Additionally, an unintended leakage of hydrogen peroxide through the atomizers before the beginning of the decontamination cycle can occur when filling the supply lines. Due to possible decontamination liquid residue in the supply lines after emptying of said supply lines, the determination of the total volume of dispensed decontamination liquid is also prone to error. Moreover, the preparations and follow-ups of the actual decontamination cycle are time-consuming.

From EP 2 786 811 A1, a device for supplying consumers with cleaning and/or disinfection fluid for preferred use in beverage bottling lines is known, the fluid being conveyed from a reservoir to the consumers via a ring conduit by means of which the excess fluid can return to the reservoir. For the use according to the object of the known device, the determination of the exact volume of the fluid dispensed to the consumers is irrelevant.

With respect to the state of the art, reference is also made to EP 1 764 115 A1 and US 2013/004390 A1.

SUMMARY OF THE INVENTION

Starting from the aforementioned state of the art, the object of the invention is to indicate an improved decontamination assembly, in particular for pharmaceutical applications, and an improved decontamination method which allows in particular for a simplified and more precise determination of the total volume of dispensed decontamination liquid. Furthermore, the distribution of the decontamination liquid aerosol in the chamber to be decontaminated is preferably to be improved and/or accelerated. Additionally, the object is to indicate an improved isolator system.

Concerning the decontamination assembly, said object is attained by the features disclosed herein.

Concerning the decontamination method, the object is attained by the features disclosed herein.

Concerning the isolator system, the object is attained by the features disclosed herein.

Advantageous embodiments of the invention are disclosed in the dependent claims. All combinations of at least two features disclosed in the description, the claims and/or the FIGURES constitute part of the scope of the invention.

In order to avoid repetitions, disclosed herein and features relating to the device are also seen as relating to the method and are thus also claimable therefor. In the same manner, disclosed features relating to the method are also seen as relating to the device and are thus also claimable therefor.

The idea of the invention in contrast to the state of the art is to supply individual atomizers with decontamination liquid, in particular hydrogen peroxide, from a decontamination liquid storage tank not by means of separate supply lines which end at the respective atomizers, but by establishing a fluid communication between several atomizers disposed in the chamber to be decontaminated and a (common) ring conduit, i.e. a conduit which discharges from the decontamination liquid storage tank and which discharges into said decontamination liquid storage tank at the end or outlet side, decontamination liquid from the decontamination liquid storage tank thus being conveyable through the ring conduit in a circle and the decontamination liquid thus flowing back into the (common) decontamination liquid storage tank after flowing through the ring conduit. At the same time, the ring conduit is assigned pressure adjustment means by means of which the liquid pressure in the ring conduit can be kept in a predefined liquid pressure range, in particular between 0.05 bar and 0.8 bar, particularly preferably between 0.1 bar and 0.8 bar, more preferably between 0.1 bar and 0.5 bar, particularly preferably between 0.2 bar and 0.5 bar. Depending on the used atomizers, the pressure range can be defined in a different manner. When dispensing decontamination liquid by means of the atomizers, the pressure in the ring conduit is preferably permanently higher than 0 bar in order to ensure that a sufficient volume of decontamination liquid is applied or can be applied to all atomizers.

By providing a ring conduit, the filling of the conduit, which is difficult to control in the state of the art, is simplified because the ring conduit is completely filled with decontamination liquid in a reliable manner when the decontamination liquid returns to the decontamination liquid storage tank on the outlet side. A displacement of air out of the ring conduit by means of the atomizers into the chamber to be decontaminated is not required. Furthermore, essentially similar liquid pressure conditions can be realized at all atomizers by providing the ring conduit. By providing the ring conduit, the determination of the total volume of decontamination liquid dispensed into the chamber to be decontaminated by means of the atomizers can be realized in a very precise and simpler manner compared to the state of the art because an emptying of the supply line realized as a ring conduit is not required. Instead, the difference can be defined between the weight of the decontamination liquid storage tank when the ring conduit is filled before the decontamination cycle, i.e. before the atomization process, and the weight of the decontamination liquid storage tank when the ring conduit is (still) filled with decontamination liquid after the decontamination cycle, i.e. after the atomization process. An emptying of the ring conduit for determining the dispensed decontamination liquid volume is no longer required. However, it is conceivable and preferable to empty the ring conduit after a decontamination cycle or before a new decontamination cycle, in particular to empty said ring conduit by means of compressed air, as will be described below, in order to avoid decontamination liquid residue in the ring conduit over a long period of time; however, since said optional step of the method is no longer required for validating the process or for determining the dispensed decontamination liquid volume, possible minimum liquid residue after the emptying are irrelevant with respect to the accuracy of the determined dispensed decontamination liquid volume.

The pressure adjustment means which are assigned to the ring conduit according to the invention are used in order to keep the liquid pressure in the ring conduit in a predefined or defined range. This ensures essentially similar flow or pressure conditions at the atomizers which are connected to the ring conduit. The atomizers which are connected to the ring conduit are preferably equidistantly spaced apart from the ring conduit in order to, at least largely, prevent different line lengths between the ring conduit and the atomizers. Furthermore, the pressure adjustment means in combination with the ring conduit allow for a definition of the decontamination liquid volume dispensed into the chamber to be decontaminated by means of all atomizers and/or individual atomizers and/or groups of atomizers by simply defining the opening and closing time of the valve means due to the essentially constant liquid pressure conditions at the atomizers which are connected to the ring conduit. As provided in an advantageous embodiment of the invention, this allows for the realization of the valve means as switch valves which are operated particularly preferably in an intermittent manner (pulsed or cycled), the opening and closing time of the switch valves, which is or can be clocked, defining the decontamination liquid volume dispensed at a given liquid pressure in the ring conduit.

The conveyed volume flow rate is preferably set in such a manner, in particular by adjusting or defining the pump capacity and by adjusting or defining the pressure adjustment means, that a volume flow rate which is conveyed to the ring conduit is higher than the total volume flow rate which is dispensed by means of the atomizers at the same time, decontamination liquid thus always flowing out of the ring conduit back into the storage tank during the atomization. This is also used for control or as a guarantee that all atomizers connected to the ring conduit are or can be supplied with decontamination liquid.

The flow of decontamination liquid from the ring conduit towards the atomizers can therefore be influenced by the valve means disposed between the atomizers and the ring conduit; in particular, a fluid communication can be established and interrupted. As has already been mentioned and will be described in greater detail below, the valve means preferably comprise a plurality of valves, in particular switch valves which switch in a discrete manner, preferably in the form of 2/2 way valves, such a valve being preferably disposed between individual atomizers, in particular all atomizers, and the ring conduit assigned thereto and/or between the ring conduit and at least one group of atomizers. If several groups of atomizers disposed at the ring conduit are provided, such a valve is preferably assigned to each group. In order to control and influence the production of the decontamination liquid aerosol in an optimum manner, however, each atomizer is preferably assigned an individual valve, in particular a switch valve, i.e. a valve which can be switched between a completely closed and a completely opened valve position.

The valves are particularly preferably disposed as close to the ring conduit as possible, preferably directly adjacent to said ring conduit.

A decontamination liquid line length between several atomizers, in particular all atomizers, and the valves (valve means) assigned thereto and/or the ring conduit is preferably as short as possible and is preferably less than 50 cm, more preferably less than 40 cm, even more preferably less than 30 cm, even more preferably less than 20 cm or than 10 cm, particularly preferably less than 5 cm, measured in the direction of flow of the decontamination liquid from the ring conduit towards the respective atomizer. The line length is preferably reduced close to zero. In a preferred embodiment, if a line length is provided between the respective valve and the corresponding atomizer, it is conceivable to empty said line by means of compressed air out of the ring conduit into the chamber to be decontaminated by means of the respective atomizer, in particular at the end of a decontamination process (preferably after a weighing process of the decontamination liquid in the storage tank).

During a decontamination process, between 5 g and 10 g, in particular 7.5 g of decontamination liquid per cubic meter of chamber to be decontaminated are preferably atomized out of the ring conduit into the chamber to be decontaminated by means of the atomizers as a whole using the decontamination assembly and/or the decontamination method.

The decontamination assembly is preferably configured in such a manner or the decontamination method is preferably realized in such a manner that, during a decontamination cycle, i.e. as the decontamination liquid is being dispensed to the atomizers by means of the ring conduit, decontamination liquid flows back into the decontamination liquid storage tank via the ring conduit in a periodical or continuous manner, i.e. that it is conveyed in a circle.

As provided within the scope of the invention, it is generally possible that the decontamination assembly has several chambers to be decontaminated. In this regard, it is possible to assign ring conduits comprising corresponding atomizers to individual chambers. Furthermore, an alternative embodiment can be realized in which one ring conduit is guided through several chambers to be decontaminated in such a manner that atomizers disposed in the different chambers to be decontaminated can be or are supplied with decontamination liquid from the decontamination liquid storage tank by means of said common ring conduit. Additionally, it is possible to realize an embodiment in which a single chamber to be decontaminated is assigned a ring conduit by means of which several atomizers disposed in the chamber to be decontaminated can be or are supplied with decontamination liquid.

As indicated above, the total volume of decontamination liquid dispensed to the atomizers during a decontamination cycle can be determined in a simple and fast manner by means of the decontamination assembly according to the invention and the decontamination method according to the invention. According to the invention, the decontamination assembly comprises corresponding measuring means and said means are used within the scope of the method. The measuring means preferably comprise weighing means, in particular in the form of a weighing scale, for determining a decontamination liquid volume in the decontamination liquid storage tank. In the simplest case, the total volume of dispensed decontamination liquid can be determined in a manual manner by reading a measurement result (weight) of the decontamination liquid storage tank (when the ring conduit is filled) before and after a decontamination liquid cycle and by defining the difference or by setting the weighing means to zero (tare) when the ring conduit is filled before a decontamination liquid cycle and by reading the dispensed decontamination liquid volume, i.e. its weight, after a decontamination cycle when the ring conduit is filled. Alternatively, the measuring means can preferably be configured to be automated, the measuring means being configured to determine the total volume of decontamination liquid dispensed to the atomizers by defining the difference between the weight of the decontamination liquid volume in the decontamination liquid storage tank when the ring conduit is filled with decontamination liquid before the decontamination cycle and the weight of the decontamination liquid volume in the decontamination liquid storage tank when the ring conduit is filled with decontamination liquid after the decontamination cycle.

With respect to the configuration of the pressure adjustment means, different possibilities are available. In principle, it is possible to use an electronic control system which measures an actual pressure in the ring conduit by means of corresponding measuring means and takes said actual pressure into account when controlling the pressure towards a target pressure, the control system comprising a proportional valve, in particular an electromagnetic proportional valve or, in particular, a PWM-controlled switch valve controlled in a cyclic manner, which can be or is controlled in a corresponding manner, preferably as an actuator, by means of which decontamination liquid is conveyed to the decontamination liquid storage tank in a controlled manner in order to limit the pressure. Additionally or alternatively, it is possible to adjust the pressure by means of a corresponding pump control if the pump is configured and controlled in a corresponding manner. Concerning the realization of a pump control, in particular, it is possible to dispense with a controlled conveyance of decontamination liquid towards the decontamination liquid storage tank during the decontamination cycle, a combination of pump control and controlled conveyance also being possible, of course. As will be described below, it is also possible to convey the decontamination liquid (with or preferably without pump control) into the decontamination liquid storage tank during the decontamination cycle in a controlled manner by means of a non-return valve or control valve which operates in a mechanical manner.

In a particularly preferred embodiment, the pressure adjustment means comprise a non-return valve, in particular in the ring conduit, particularly preferably at the end of said ring conduit or downstream of the junctions for the atomizers in the direction of flow of the decontamination liquid in the ring conduit, the valve element of said non-return valve being configured to open the non-return valve or the ring conduit towards the decontamination liquid storage tank against the spring force of a return spring in order to thus convey decontamination liquid into the decontamination liquid storage tank in a controlled manner to adjust or limit the pressure. In other words, the pressure adjustment means comprise a non-return valve which operates in a mechanical manner and is therefore solid and fast-acting and which controls the liquid pressure in the ring conduit in an automatic manner in cooperation with the (conveyor) pump, which generates a conveying pressure, in particular by limiting the liquid pressure to a maximum value by varying the degree of opening of the non-return valve towards the decontamination liquid storage tank. An additional control of the conveyed volume of the pump is not required (and preferably not realized)—said pump is preferably supplied or operated with a constant electric power.

In general, in particular when the pressure control means are realized as a non-return valve, the pressure control means are preferably configured and tuned to the pump, in particular to a constant pump capacity, in such a manner, preferably by setting and/or defining (dimensioning) the operating point of the pressure control means, in particular of the non-return valve which operates in a mechanical manner, that decontamination liquid flows, i.e. is conveyed in a controlled manner, through the outlet of the ring conduit back into the decontamination liquid storage tank when the valve means are opened, i.e. when decontamination liquid is dispensed to the chamber to be decontaminated by means of the atomizers. As a result, pressure variations which would occur if the pressure control means were completely closed are reliably prevented.

As already indicated above, the pressure adjustment means provided according to the invention in combination with the ring conduit allow for an adjustment or a definition of the dispensed volume of decontamination liquid by means of the atomizers by using simple and solid switch valves, in particular 2/2 way valves, by defining the opening and closing time of the switch valves or valve means by means of the control means. In a particularly preferred embodiment, individual atomizers, preferably all atomizers, are assigned such a switch valve in order to supply the respective atomizer with decontamination liquid from the ring conduit. Alternatively, if several atomizers are grouped, it is conceivable to assign a switch valve, in particular a single switch valve, to said group of atomizers. If several groups are provided, such a switch valve, which is disposed between the atomizers and the ring conduit, is preferably assigned to each group, in particular to all groups. The production of aerosol and the dispensed decontamination liquid volume per atomizer can be influenced in an optimum manner if each atomizer is assigned such a switch valve.

In principle, it is possible that several or individual switch valves, in particular all switch valves, are left open during an entire decontamination cycle or for a specified period (period of time) or for several subsequent periods of time of the decontamination cycle. In a particularly preferred embodiment, however, at least one of the switch valves, in particular several switch valves, more preferably all switch valves are operated or driven by the control means in an intermittent manner (cycled or pulsed). All switch valves can be controlled in the same manner—in a preferred embodiment, at least two of the switch valves are controlled differently, i.e. with different opening and closing times, in order to cause different dispensed volumes of decontamination liquid by means of the atomizers which are assigned to the switch valves, in particular in order to apply a larger volume of decontamination liquid aerosol to areas of the chamber to be decontaminated which are particularly crucial or susceptible to infection. Additionally, it is possible to operate or to open several switch valves or groups of switch valves in a sequential manner, in particular in a pulsed manner, in order to cause a flow of aerosol in the chamber to be decontaminated, so that an improved distribution of the decontamination liquid aerosol in the chamber to be decontaminated can be ensured.

As indicated above, the distance between the atomizers and the ring conduit, i.e. the respective line length, is as short as possible and/or at least approximately the same for all atomizers. The switch valves are particularly preferably disposed directly adjacent to the ring conduit and the atomizers directly adjoin the corresponding switch valve.

Concerning the specific realization of the atomizers, different possibilities are available. It is conceivable in general to use ultrasonic atomizers or other atomizers which operate on the basis of other physical active principles. In a particularly preferred embodiment, two-component nozzles (mixing nozzles) are used as atomizers and are connected to a gas pressure source, in particular a compressed air source, to generate a carrier gas flow, the decontamination liquid volume which is required for producing the desired aerosol being added to the carrier gas flow, in particular in a pulsed (cycled) or intermittent manner, by means of the valve means, in particular the corresponding switch valve. Alternatively, in particular for smaller chambers to be decontaminated, it is possible to use single-component nozzles, which are also preferably operated or supplied with decontamination liquid in a pulsed manner. The atomizers are preferably configured in such a manner that 90% of the decontamination mist or aerosol droplets leaving the atomizers have a particle size of less than 20 µm, preferably less than 10 µm.

In a particularly preferred embodiment, a connector valve is disposed downstream of the pump in the ring conduit in order to bypass two ring conduit sections when the connector valve is opened. In this way, a conveying pressure can be applied to the ring conduit and thus to the atomizers from two sides of the ring conduit by means of the pump, thus ensuring more consistent pressure conditions. The bypass line preferably joins the ring conduit in an area at the end of the ring conduit upstream of the pressure adjustment means. In other words, the bypass line short-circuits a ring conduit section to which the atomizers are directly connected by means of the valve means.

Notwithstanding the above, the pressure adjustment means can preferably be bypassed by means of a bypass valve in order to rinse and/or to empty the ring conduit by means of compressed air in an improved manner. Irrespective of this, the ring conduit is preferably assigned a compressed gas connection, in particular a compressed air connection, for emptying the ring conduit. The compressed air connection can also be used in order to monitor the ring conduit for leakage before a decontamination cycle by applying compressed gas, in particular compressed air, to the ring conduit and by monitoring a possible pressure drop, in particular by means of a corresponding pressure monitoring device which is assigned to the ring conduit.

The invention also relates to an isolator system comprising an aforementioned decontamination assembly, the chamber to be decontaminated being a chamber of said isolator, in particular a manipulator chamber and/or a plenum chamber separated from the manipulator chamber by a membrane for laminarizing a circulation air flow of a circulation fan. A handling device for handling, in particular producing, dosing and/or filling a pharmaceutical or medicinal ingredient is preferably located inside the manipulator chamber.

Furthermore, the invention relates to a decontamination method. According to the invention, atomizers which are in fluid communication with a ring conduit by means of the valve means, in particular switch valves, said ring conduit having an inlet and a separate outlet, are supplied with decontamination liquid by conveying decontamination liquid from the decontamination liquid storage tank into the inlet by means of a pump and by letting the conveying liquid flow back into the decontamination liquid storage tank through the outlet, in particular during a decontamination cycle, i.e. when decontamination liquid is being dispensed by means of the atomizers, a liquid pressure of the decontamination liquid in the ring conduit being kept in a predefined range, in particular limited to a maximum pressure, by means of pressure adjustment means, the pump ensuring the corresponding pressurization.

If, as is preferred, the ring conduit has been emptied, for example by means of compressed air, said ring conduit is completely filled with decontamination liquid from the decontamination liquid storage tank before the beginning of a decontamination cycle.

Within the scope of the method, the valve means, which are preferably configured as switch valves, are controlled by control means in a timed manner in such a manner that the opening and/or closing time of the switch valves during a decontamination cycle is predefined in order to predefine the volume of decontamination liquid to be dispensed by means of the atomizers. The switch valves are preferably operated in a cycled, i.e. intermittent manner, i.e. in such a manner that said switch valves can be switched between a closed and a, preferably completely, opened switching state in an alternating manner. By assigning a specific opening and/or closing time to the individual valves of the valve means, a desired, in particular even distribution of the decontamination liquid aerosol can be ensured.

In particular, individual atomizers or groups of atomizers can also be operated in a periodical manner, in particular in a cycled or intermittent manner in each active period, in order to influence the distribution of the aerosol.

A gas or air pressure regulating device for regulating the gas pressure, in particular the air pressure, in the chamber to be decontaminated is preferably active during the decontamination cycle in order to ensure constant gas pressure conditions during the decontamination.

Additional preferred embodiments and details of the method are described in the description of the decontamination assembly and of the isolator system.

BRIEF DESCRIPTION OF THE DRAWINGS

Further advantages, features and details of the invention can be derived from the following description of a preferred exemplary embodiment and from the drawing.

DETAILED DESCRIPTION

FIG. 1 is a fluid scheme of a preferred exemplary embodiment of a decontamination assembly which is configured according to the idea of the invention and in which the chamber to be decontaminated is an isolator chamber, preferably a manipulator chamber.

In FIG. 1, an isolator system 1 comprising an isolator 2 for pharmaceutical applications and a decontamination assembly 3 for decontaminating a chamber to be decontaminated 4 being assigned to or integrated into isolator 2 are shown, said chamber 4 being a so-called manipulator chamber of isolator 2, in which a pharmaceutical process such as a dosing, production and/or filling process takes place by means of corresponding machinery or equipment, the manipulator chamber being manually accessible by means of glove ports (not shown). In a manner known per se, the manipulator chamber is connected, via backflow channels, to a circulation generating chamber which is disposed above the chamber to be decontaminated and in which a circulation fan is located, a circulation volume flow being producible by means of the circulation fan when isolator 2 is operated, said circulation volume flow flowing from the circulation chamber via corresponding high efficiency particulate air filters into a so-called plenum chamber and via said plenum chamber through a membrane into the manipulator chamber. The aforementioned backflow channels are preferably disposed between two transparent panes, in particular transparent glass panes.

In the case at hand, the decontamination assembly comprises several atomizers A, B, C, D which are configured as two-component nozzles (mixing nozzles). For this purpose, each atomizer A, B, C, D is connected to a corresponding compressed air supply line 5, 6, 7, 8 which can be supplied with compressed air from a compressed air source 9. In the case at hand, compressed air supply lines 5, 6, 7, 8 are connected to a compressed air distribution line 10 by means of which chamber 4 to be decontaminated can be supplied with pure and conditioned (temperature-controlled and/or moisture-regulated) compressed air, as well.

In the case at hand, each compressed air supply line 5, 6, 7, 8 is assigned a pressure measuring device 11, 12, 13, 14 in order to monitor the respective air pressure. Furthermore, a stop valve 15, 16, 17, 18 is disposed in each compressed air supply line 5, 6, 7, 8 in order to be able to stop or to open a connection between a respective atomizer A, B, C, D and compressed air source 9. The air pressure (supply air pressure) at individual atomizers A, B, C, D can be or is defined by means of corresponding throttles or adjusting valves 19, 20, 21, 22. Additionally, there is a filter 23, 24, 25, 26 in each compressed air supply line 5, 6, 7, 8. In any event, atomizers A, B, C, D are supplied with a compressed air carrier air flow to which, as will be described below, decontamination liquid is added, preferably in an intermittent manner, said decontamination liquid being micro-dispersed or nebulized by means of atomizers A, B, C, D, which are located in chamber to be decontaminated 4, by producing a corresponding decontamination liquid aerosol.

Valve means 27 are disposed upstream of atomizers A, B, C, D in the form of switch valves 28, 29, 30, 31 in the case at hand, which can be controlled in a timed manner by means of control means (not shown) to influence the respective opening and closing time in order to define the volume of decontamination liquid dispensed to atomizers A, B, C, D. In the present exemplary embodiment, switch valves 28, 29, 30, 31 are operated in an intermittent, i.e. clocked manner. The total opening time of individual switch valves 28, 29, 30, 31 is defined by means of control means to define the decontamination liquid volume to be dispensed. The illustration according to FIG. 1 shows that atomizers A, B, C, D are directly adjacent to switch valves 28, 29, 30, 31. Switch valves 28, 29, 30, 31 are directly adjacent to a ring conduit 32 and control the dispensation of decontamination liquid from said ring conduit to the assigned atomizers.

As explained in the general description, switch valves 28, 29, 30, 31 can be controlled in the same manner or in different manners, for example in a sequential or overlapping manner, in order to influence the decontamination aerosol flow in chamber to be decontaminated 4.

Ring conduit 32 comprises an inlet 33 and a separate outlet 34, decontamination liquid from a decontamination liquid storage tank 36 being conveyed into inlet 33 by means of a pump 35. Decontamination liquid thus arrives at switch valves 28, 29, 30, 31 and, by means of said switch valves, at assigned atomizers A, B, C, D. The decontamination liquid flows through outlet 34 back into decontamination liquid storage tank 36, i.e. it is conveyed in a circular manner.

Ring conduit 32 is assigned pressure adjustment means 37 comprising, in the case at hand, a non-return valve 38 which operates in a mechanical manner and which is tuned to the, in particular constant, pump capacity of pump 35 in such a manner that decontamination liquid which is converted into an aerosol by means of at least one of atomizers A, B, C, D flows back into decontamination liquid storage 36 during a decontamination cycle.

During the decontamination cycle, a bypass valve for a possible bypassing of non-return valve 38 is closed.

Decontamination liquid storage tank 36 is assigned measuring means 40 which are in the form of weighing means 41 in the case at hand and which can be used to determine the weight of the decontamination liquid located in decontamination liquid storage tank 36 when ring conduit 32 is filled with decontamination liquid before a decontamination cycle and the weight of the decontamination liquid located in decontamination liquid storage tank 36 when ring conduit 32 is filled after completion of the decontamination cycle.

A connector valve 42 is optionally provided, a starting section and an end section of ring conduit 32 being connectable by means of said connector valve 42 so that, in particular during a decontamination cycle, pump 35 can convey decontamination liquid from two sides into a section of ring conduit 32 from which atomizers A, B, C, D can be supplied or to which atomizers A, B, C, D are connected via valve means 27.

Furthermore, ring conduit 32 is assigned a compressed air connection 43 for emptying ring conduit 32, for which purpose the line connections are switchable in a corresponding manner by means of provided 3/2 way valves 44, 45.

As can be seen, ring conduit 32 is assigned a fluid pressure measuring device 46. In the case at hand, said device 46 is only used for monitoring the liquid pressure in ring conduit 32 and is not part of a pressure control—in the present exemplary embodiment, the pressure adjustment of the fluid pressure is exclusively realized through an interaction of pump 35 and non-return valve 38, alternative solutions for adjusting the pressure or for keeping the pressure in a desired range also being conceivable, as is explained in the general description.

REFERENCE SIGNS 1 isolator system (system)
2 isolator
3 decontamination assembly
4 chamber to be decontaminated
5 compressed air supply line
6 compressed air supply line
7 compressed air supply line
8 compressed air supply line
9 compressed air source
10 compressed air distribution line
11 pressure measuring device
12 pressure measuring device
13 pressure measuring device
14 pressure measuring device
15 stop valve
16 stop valve
17 stop valve
18 stop valve
19 adjusting valve
20 adjusting valve
21 adjusting valve
22 adjusting valve
23 filter
24 filter
25 filter
26 filter
27 valve means
28 switch valve
29 switch valve
30 switch valve
31 switch valve
32 ring conduit
33 inlet of the ring conduit
34 outlet of the ring conduit
35 pump
36 decontamination liquid storage tank
37 pressure adjustment means
38 non-return valve
39 bypass valve
40 measuring means
41 weighing means
42 connector valve
43 compressed air connection
44 3/2 way valve
45 3/2 way valve
46 fluid pressure measuring device
A atomizer
B atomizer
C atomizer
D atomizer

The invention claimed is:

1. A decontamination assembly for pharmaceutical applications, comprising:
   at least one chamber to be decontaminated (4),
   a decontamination liquid storage tank (36) by which a plurality of atomizers (A, B, C, D) disposed in the at least one chamber to be decontaminated (4) for producing a decontaminant aerosol can be supplied with decontamination liquid,
   valve means (27) for supplying the decontamination liquid to the plurality of atomizers (A, B, C, D), wherein the valve means can be controlled by means of electronic control means, the plurality of atomizers (A, B, C, D) being in fluid communication with a ring conduit (32) having an inlet (33) and a separate outlet (34) by means of the valve means (27), decontamination liquid from the decontamination liquid storage tank (36) being conveyable into the inlet of said ring conduit by means of a pump (35) and decontamination liquid flowing out of the outlet of said ring conduit back into the decontamination liquid storage tank (36),
   pressure adjustment means (37) for keeping the pressure in the ring conduit (32) at a predefined liquid pressure range assigned to the ring conduit (32), and
   measuring means (40) for determining a total volume of decontamination liquid dispensed to the plurality of atomizers (A, B, C, D) during a decontamination cycle,
   the decontamination assembly being configured in such a manner that between 5 g and 10 g of decontamination liquid per cubic meter of the at least one chamber to be decontaminated is atomized by all atomizers from the ring conduit into the at least one chamber to be decontaminated during a decontamination cycle and the plurality of atomizers being realized in such a manner that 90% of the decontamination mist or aerosol droplets leaving the plurality of atomizers have a particle size of less than 20 μm.

2. The decontamination assembly according to claim 1, wherein the measuring means (40) are configured to determine the total volume of the decontamination liquid dispensed to the plurality of atomizers by defining the difference between the weight of the decontamination liquid volume in the decontamination liquid storage tank (36) when the ring conduit (32) is filled with decontamination liquid before the decontamination cycle and the weight of the decontamination liquid volume in the decontamination liquid storage tank (36) when the ring conduit (32) is filled with decontamination liquid after the decontamination cycle.

3. The decontamination assembly according to claim 1, wherein the pressure adjustment means (37) comprise a non-return valve (38) disposed in the ring conduit (32), the valve means being configured to open the non-return valve (38) towards the decontamination liquid storage tank (36) against the spring force of a return spring.

4. The decontamination assembly according to claim 1, wherein the pressure adjustment means (37) are configured and tuned to the pump (35) in such a manner that the decontamination liquid flows through the outlet (34) back into the decontamination liquid storage tank (36) when the valve means (27) are opened.

5. The decontamination assembly according to claim 1, wherein the valve means (27) comprise switch valves (28, 29, 30, 31), which can be controlled in a cyclic manner, in order to supply a respective atomizer of the plurality of atomizers (A, B, C, D) with decontamination liquid from the ring conduit (32) and/or wherein at least one group of atomizers of the plurality of atomizers (A, B, C, D) is/are assigned a switch valve (28, 29, 30, 31).

6. The decontamination assembly according to claim 5, wherein the electronic control means are configured to control the switch valves (28, 29, 30, 31) in such a manner that a plurality of the switch valves (28, 29, 30, 31) or groups of switch valves are simultaneously opened and/or are operated in a cycled manner and/or in such a manner that a plurality of the switch valves (28, 29, 30, 31) or the groups of switch valves are subsequently opened and/or are operated in a cycled manner and/or in such a manner that at least one of the switch valves (28, 29, 30, 31) or at least one of the groups of switch valves is opened for a longer period of time and/or operated in a cycled manner for a longer period of time during a decontamination cycle than at least one other switch valve (28, 29, 30, 31) or one other group of switch valves.

7. The decontamination assembly according to claim 5, wherein the electronic control means are configured to control the switch valves (28, 29, 30, 31) in such a manner that a given total volume of decontamination liquid to be atomized can be dosed by controlling a clocked total opening time of the switch valves (28, 29, 30, 31) and/or in such a manner that a given volume of decontamination liquid to be dosed can be dosed at least one of the plurality of atomizers (A, B, C, D) or a group of the plurality of atomizers (A, B, C, D) by controlling a clocked opening time of a corresponding switch valve (28, 29, 30, 31).

8. The decontamination assembly according to claim 5, wherein the switch valves (28, 29, 30, 31) are 2-/2-way valves, and wherein individual atomizers of the plurality of atomizers (A, B, C, D) are assigned the switch valve (28, 29, 30, 31).

9. The decontamination assembly according to claim 1, wherein at least two of the plurality of atomizers (A, B, C, D) which are connected to the ring conduit (32) are equidistantly spaced apart from the ring conduit (32).

10. The decontamination assembly according to claim 9, wherein a majority of the plurality of atomizers (A, B, C, D) which are connected to the ring conduit (32) are equidistantly spaced apart from the ring conduit (32).

11. The decontamination assembly according to claim 9, wherein all atomizers of the plurality of atomizers (A, B, C, D) which are connected to the ring conduit (32) are equidistantly spaced apart from the ring conduit (32).

12. The decontamination assembly according to claim 1, wherein the plurality of atomizers (A, B, C, D) are configured as two-component nozzles and are connected to a gas pressure source, in a gas-conducting manner to generate a carrier gas flow for the decontaminant aerosol to be produced.

13. The decontamination assembly according to claim 1, wherein the ring conduit (32) is assigned a connector valve (42) behind the pump (35) in order to establish and close a bypass between an area of the ring conduit (32) in front of and behind the plurality of atomizers (A, B, C, D) and/or wherein the pressure adjustment means (37) can be bypassed by means of a bypass valve (39) and/or wherein the ring conduit (32) is assigned a compressed gas connection, for emptying the ring conduit (32).

14. The decontamination assembly according to claim 1, wherein the at least one chamber is an isolator chamber.

15. The decontamination assembly according to claim 1, wherein the at least one chamber is a manipulator chamber and/or a plenum chamber separated from the manipulator chamber by a membrane.

16. The decontamination assembly according to claim 1, wherein the plurality of atomizers (A, B, C, D) are configured as two-component nozzles for producing a decontaminated aerosol.

17. The decontamination assembly according to claim 1, wherein the decontamination liquid is hydrogen peroxide.

18. The decontamination assembly according to claim 1, the measuring means (40) comprises weighing means (41) for determining a decontamination liquid volume in the decontamination liquid storage tank (36).

19. The decontamination assembly according to claim 1, wherein the plurality of atomizers (A, B, C, D) are configured as two-component nozzles supplied with compressed air.

20. A system comprising an isolator (2), comprising a chamber to be decontaminated (4), and comprising a decontamination assembly (3) according to claim 1.

21. The system according to claim 20, wherein the isolator (2) is an isolator for pharmaceutical applications, and wherein the chamber to be decontaminated is a manipulator chamber and/or a plenum chamber separated from the manipulator chamber by a membrane for laminarizing an airflow of a circulation fan.

22. A decontamination method for operating a decontamination assembly (3) according to claim 1, comprising:
  decontaminating the chamber to be decontaminated (4) by producing the decontaminant aerosol from the decontamination liquid by means of the atomizers (A, B, C, D) which are disposed in the chamber to be decontaminated (4),
  supplying said atomizers with the decontamination liquid from the decontamination liquid storage tank (36) via the valve means (27), the atomizers (A, B, C, D) being in fluid communication with the ring conduit (32) having the inlet (33) and the separate outlet (34),
  conveying the decontamination liquid from the decontamination liquid storage tank (36) into the inlet of said ring conduit by means of the pump (35) and
  flowing the decontamination liquid out of the outlet of said ring conduit back into the decontamination liquid storage tank (36),
  keeping a liquid pressure of the decontamination liquid in the ring conduit (32) at a predefined pressure range by means of the pressure adjustment means (37),
  determining a total volume of the decontamination liquid dispensed to the atomizers (A, B, C, D) by defining a difference between the weight of the decontamination liquid volume in the decontamination liquid storage tank (36) when the ring conduit (32) is filled with decontamination liquid before the decontamination cycle and the weight of the decontamination liquid volume in the decontamination liquid storage tank (36) when the ring conduit (32) is filled with decontamination liquid after the decontamination cycle, the decontamination method atomizing between 5 g and 10 g, of the decontamination liquid per cubic meter of the chamber to be decontaminated by all the atomizers from the ring conduit into the chamber to be decontaminated during a decontamination cycle and 90% of the decontamination mist or aerosol droplets leaving the atomizers having a particle size of less than 20 μm.

23. The decontamination method according to claim 22, wherein the ring conduit (32) is filled completely with the decontamination liquid from the decontamination liquid storage tank (36) by means of the pump (35) before the decontamination liquid flows from the ring conduit (32) to the atomizers (A, B, C, D) in a decontamination cycle by a corresponding control of the valve means (27).

\* \* \* \* \*